(12) United States Patent
Gohno

(10) Patent No.: US 7,050,532 B2
(45) Date of Patent: May 23, 2006

(54) IMAGING CONDITION DETERMINING METHOD AND AN X-RAY CT APPARATUS

(75) Inventor: Makoto Gohno, Tokyo (JP)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 0 days.

(21) Appl. No.: 10/924,365

(22) Filed: Aug. 23, 2004

(65) Prior Publication Data
US 2005/0053190 A1 Mar. 10, 2005

(30) Foreign Application Priority Data
Sep. 5, 2003 (JP) ............................. 2003-313774

(51) Int. Cl.
H05G 1/34 (2006.01)
(52) U.S. Cl. .......................................... 378/8; 378/108
(58) Field of Classification Search ................ 378/16, 378/4, 901, 108, 114–117, 8
See application file for complete search history.

(56) References Cited

U.S. PATENT DOCUMENTS

| 4,160,906 A | 7/1979 | Daniels et al. |
| 4,945,476 A | 7/1990 | Bodick et al. |

(Continued)

FOREIGN PATENT DOCUMENTS

| EP | 1354554 A2 | 10/2003 |
| JP | 09-299360 | 11/1997 |
| JP | 2003-044588 | 2/2003 |
| JP | 2003-079611 | 3/2003 |

OTHER PUBLICATIONS

European Patent Office Search Report; 153401/10130; 04255283.6-2305-; GE Medical Systems Global Technology Company LLC; 3 pgs.

(Continued)

Primary Examiner—David V. Bruce
Assistant Examiner—Hoon Song
(74) Attorney, Agent, or Firm—Carl B. Horton, Esq.; Armstrong Teasdale LLP (57) ABSTRACT

An imaging condition determining method for an x-ray CT apparatus for performing imaging by a helical scan. The method includes making a table of various imaging conditions in advance, extracting at least one imaging condition from the table in accordance with age, imaging region, imaging length of the patient as well as the highest-priority objective specified by a user, and displaying the exposure dose of the patient under the at least one imaging condition, enabling the user to adjust the exposure dose, and determining the imaging condition adjusted in response to the adjustment of the exposure dose to the at least one imaging condition.

16 Claims, 10 Drawing Sheets (503)

U.S. PATENT DOCUMENTS

| | | |
|---|---|---|
| 5,233,519 A | 8/1993 | Ito |
| 5,588,036 A | 12/1996 | Fujise et al. |
| 5,807,256 A | 9/1998 | Taguchi et al. |
| 5,963,136 A | 10/1999 | O'Brien |
| 6,150,942 A | 11/2000 | O'Brien |
| 6,404,844 B1 | 6/2002 | Horiuchi et al. |
| 6,445,764 B1 | 9/2002 | Gohno et al. |
| 6,497,656 B1 | 12/2002 | Evans et al. |
| 6,501,819 B1 | 12/2002 | Unger et al. |
| 6,529,446 B1 | 3/2003 | de la Huerga |
| 6,574,166 B1 | 6/2003 | Niemiec |
| 6,859,513 B1 * | 2/2005 | Sako .................... 378/16 |
| 6,904,127 B1 * | 6/2005 | Toth et al. ............. 378/110 |
| 2003/0016778 A1 | 1/2003 | Tachizaki et al. |
| 2003/0123603 A1 * | 7/2003 | Suzuki .................... 378/4 |

OTHER PUBLICATIONS

G. Jarry et al.; A Monte Carlo-based Method to Estimate Radiaiton Dose from Spiral CT: from Phantom Testing to Patient-Specific Models; Phys. Med. Biol 48 (2003) 2645-2663.

Edward L. Nickoloff et al; Influence of Phantom Diameter, kVp and Scan Mode Upon Computed Tomography Dose Index; Med. Phys. 30 (3) Mar. 2003 pp. 395-402.

* cited by examiner

|  | candidate |
|---|---|
| DLP | 120mGycm |
| scan time | 0.5sec |
| beam thickness | 20mm |
| helical pitch | 1.25 |
| data acq. Mode | 1.25mm x 16 |
| image thickness | 2mm |
| image interval | 2mm |
| auto mA | 200 220 280 290 200 |
| kV | 120kV |
| tilt | 0deg |
| FOV | 50cm |
| total scan time | 2.5sec |

FIG. 8

|  | most appropriate condition |
|---|---|
| DLP | 100mGycm |
| scan time | 0.5sec |
| beam thickness | 10mm |
| helical pitch | 1 |
| data acq. Mode | 1.25mm x 8 |
| image thickness | 2mm |
| image interval | 2mm |
| auto mA | 200 220 230 260 280 280 320 240 210 |
| kV | 120kV |
| tilt | 0deg |
| FOV | 50cm |
| total scan time | 5sec |

FIG. 9

|  | first order candidate A | first order candidate B |
|---|---|---|
| DLP | 120mGycm | 120mGycm |
| scan time | 0.5sec | 0.5sec |
| beam thickness | 20mm | 20mm |
| helical pitch | 1.25 | 1.25 |
| data acq. Mode | 1.25mm x 16 | 1.25mm x 16 |
| image thickness | 2mm | 2mm |
| image interval | 2mm | 2mm |
| auto mA | 240 260 360 240 | 200 220 280 290 200 |
| kV | 120kV | 120kV |
| tilt | 0deg | 0deg |
| FOV | 50cm | 50cm |
| total scan time | 2sec | 2.5sec |

FIG. 10

|  | second order candidate A | second order candidate B |
|---|---|---|
| DLP | 100mGycm | 100mGycm |
| scan time | 0.5sec | 0.5sec |
| beam thickness | 20mm | 10mm |
| helical pitch | 1.25 | 1 |
| data acq. Mode | 1.25mm x 16 | 0.625mm x 16 |
| image thickness | 2mm | 2mm |
| image interval | 2mm | 2mm |
| auto mA | 200 220 300 200 | 200 220 230 260 280 280 320 290 240 210 |
| kV | 120kV | 120kV |
| tilt | 0deg | 0deg |
| FOV | 50cm | 50cm |
| total scan time | 2sec | 5sec |

IMAGING CONDITION DETERMINING METHOD AND AN X-RAY CT APPARATUS

CROSS REFERENCE TO RELATED APPLICATIONS

This application claims the benefit of Japanese Application No. 2003-313774 filed Sep. 5, 2003.

BACKGROUND OF THE INVENTION

The present invention is related to an imaging condition determining method and an X-ray CT (computed tomography) apparatus, more specifically to an imaging condition determining method for an X-ray helical scan imaging CT, and an X-ray helical scan CT apparatus.

An X-ray CT apparatus for performing helical scan imaging has imaging condition setting performed by the user prior to the imaging. The imaging condition may be set in accordance with the subject and the objective of imaging. A variety of parameters such as tube voltage, tube current, X-ray beam thickness, image slice thickness, helical pitch and so on may be set in accordance with the imaging condition. For the imaging condition selected, the exposure dose of the patient is displayed such that the operator can decide the suitability of the imaging condition (for example, see the patent document 1 below).

Patent Document 1 JP-A-2003-79611 (pp 8 to 9, and FIGS. 6 to 9)

In an X-ray CT apparatus as have been described above, if the exposure dose is not appropriate, the imaging condition is required to be revised. However it is not easy to reconfigure an alternative imaging condition consisted of a number of parameters so as to achieve the predetermined goal. In particular, the difficulty becomes increased with the cone beam characteristics elicited of the X-ray beam, along with the increase of the number of X-ray detector arrays.

In particular, when scanning with a thick beam, scan will terminate early, however the automatic control of the tube current in the direction of body axis will be unsubtle to increase the exposure dose. It is required to carefully select the thickness in accordance with the age of patient and the examination purpose.

SUMMARY OF THE INVENTION

Therefore, an object of the present invention is to realize an imaging condition determining method and an X-ray CT apparatus, which facilitate the configuration of helical scan imaging condition for the imaging conformed to the predetermined purpose.

(1) The present invention in one aspect for solving the problem includes an imaging condition determining method for an x-ray CT apparatus for performing imaging by a helical scan, comprising the steps of: making a table of various imaging condition in advance; extracting a candidate of imaging condition from the table in accordance with age, imaging region, imaging length of the patient as well as the highest-priority objective specified by a user, and displaying the exposure dose of the patient under the candidate of imaging condition; enabling the user to adjust the exposure dose; and determining the imaging condition adjusted in response to the adjustment of the exposure dose to a candidate of the imaging condition.

(2) The present invention in another aspect for solving the above cited problem includes an X-ray CT apparatus, comprising: a memory means for storing a variety of imaging condition previously made as a table; a display means for extracting a candidate of imaging condition from the table in accordance with the age, imaging region, imaging length of the patient as well as the highest-priority objective specified by the user for displaying the exposure dose of the patient under the candidate of imaging condition; an adjusting means for enabling the user to adjust the exposure dose; and a determining means for determining an imaging condition by performing correction in response to the adjustment of the exposure dose to the candidate of imaging condition.

Preferably the highest-priority objective is the exposure dose for the appropriateness of the exposure dose. Preferably the highest-priority objective is any one of exposure dose, image quality and imaging speed, for the appropriateness of the exposure dose, image quality or imaging speed. Preferably the exposure dose is indicated as DLP for the appropriateness of the exposure dose.

When there is a plurality of candidates of imaging condition, it is preferable to determine an imaging condition based on the second priority objective specified by the user for obtaining the most appropriate imaging condition. Also the second priority objective is preferably one, which is different from the highest-priority objective, of the dose, image quality and imaging speed for obtaining the most appropriate imaging condition.

The imaging condition made as a table is preferably the imaging condition based on the performance for ensuring the performance. The imaging condition made as a table is preferably the imaging condition based on a simulation for diversify the imaging condition regardless of the past record.

In the above aspects the present invention may achieve an imaging condition determining method and an X-ray CT apparatus, which facilitate the configuration of imaging condition for helical scan imaging conformed to the predetermined object, by making a table from a variety of imaging condition, extracting a candidate of imaging condition from the table in accordance with the age, imaging region and imaging length of the patient and the highest-priority objective specified by the user and display the exposure dose of patient under the selected candidate of imaging condition, enabling the user to adjust the exposure dose, and determining the final imaging condition by performing correction in response to the adjustment of said exposure dose.

Further objects and advantages of the present invention will be apparent from the following description of the preferred embodiments of the invention as illustrated in the accompanying drawings.

DETAILED DESCRIPTION OF THE INVENTION

Figure 1:
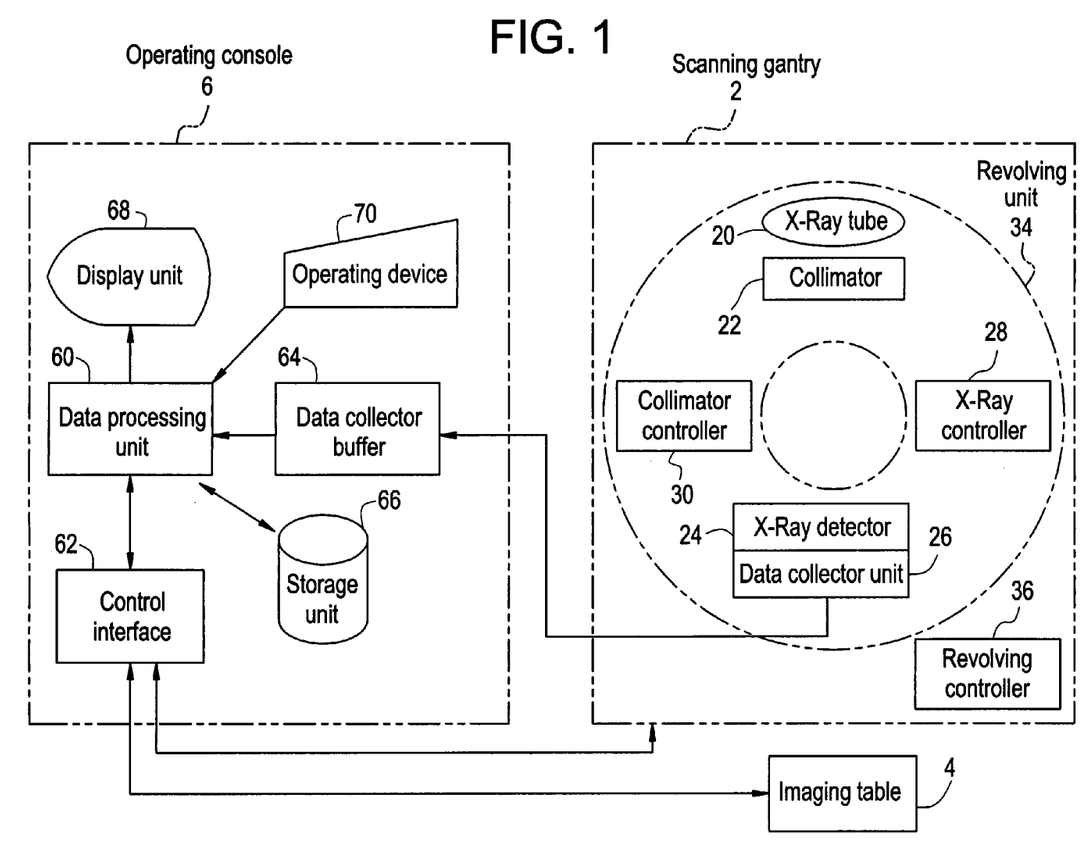
FIG. 1 is a schematic block diagram of an X-ray CT apparatus.

The best mode for carrying out the invention will be described in greater details below with reference to the drawings. FIG. 1 shows a schematic block diagram of an X-ray CT apparatus. This apparatus is an exemplary best mode carrying out the invention. The operation of this apparatus illustrates the exemplary best mode carrying out the invention with respect to the imaging condition determining method.

As shown in FIG. 1, the apparatus includes a scanning gantry 2, an imaging table 4, and an operating console 6. The scanning gantry 2 includes an X-ray tube 20. The X-ray beam emitted from the X-ray tube 20 but not shown in the figure will be collimated to an X-ray beam of the shape of cone, i.e., a cone beam X-ray by a collimator 22, to irradiate an X-ray detector 24. The X-ray detector 24 includes a plurality of detector elements arranged in an array corresponding to the sector of the X-ray beam. The structure of the X-ray detector 24 will be described later.

In the space between the X-ray tube 20 and the X-ray detector 24 a subject to be imaged is mounted on the imaging table 4 and carried. The X-ray tube 20, the collimator 22, and the X-ray detector 24 will constitute the X-ray radiation and detection system. The X-ray radiation and detection system will be described later.

The X-ray detector 24 is connected to a data collector unit 26. The data collector unit 26 will gather the detected signals from each detector element in the X-ray detector 24 as digital data. The detection signal from the detector elements will be the signal illustrative of the projection of the subject by the X-ray beam. The signal will be referred to as projection data herein below or abbreviated simply to data.

The emission of X-ray from the X-ray tube 20 is controlled by an X-ray controller 28. The connection between the X-ray tube 20 and the X-ray controller 28 is omitted in the figure. The collimator 22 is controlled by the collimator controller 30. The connection between the collimator 22 and the collimator controller 30 is omitted in the figure.

Those parts from the X-ray tube 20 to the collimator controller 30 are mounted on the revolving unit 34 of the scanning gantry 2. The rotation of the revolving unit 34 is controlled by the revolving controller 36. The connection between the revolving unit 34 and the revolving controller 36 is omitted in the figure.

The operating console 6 includes a data processing unit 60. The data processing unit 60 is constituted for example by a computer. The data processing unit 60 is connected to a control interface 62. The control interface 62 is connected to the scanning gantry 2 and the imaging table 4. The data processing unit 60 controls the scanning gantry 2 and the imaging table 4 through the control interface 62.

The data collector unit 26, the X-ray controller 28, the collimator controller 30 and the revolving controller 36 in the scanning gantry 2 are controlled through the control interface 62. The respective connection between those members and the control interface 62 is omitted in the figure.

The data processing unit 60 is connected to a data collector buffer 64. The data collector buffer 64 is connected to the data collector unit 26 of the scanning gantry 2. The data collected from the data collector unit 26 is sent through the data collector buffer 64 to the data processing unit 60.

The data processing unit 60 is connected to a storage unit 66. The storage unit 66 stores projection data input to the data processing unit 60 via the data collector buffer 64 and the control interface 62. The storage unit 66 also stores a program for the data processing unit 60. The operation of the apparatus is performed by executing the program by the data processing unit 60.

The data processing unit 60 performs the image reconstruction using the projection data collected to the storage unit 66 through the data collector buffer 64. The data processing unit 60 may be an example of the reconstruction means in accordance with the present invention. The image reconstruction may use such method as the filtered back projection.

The data processing unit 60 is connected to a display unit 68 and an operating device 70. The display unit 68 is constituted of a graphic display device or the like. The operating device 70 is constituted of a keyboard equipped with a pointing device.

The display unit 68 displays a reconstructed image output from the data processing unit 60 and any other information thereon. The operating device 70 is manipulated by the operator to input a range of instructions and information to the data processing unit 60. The operator uses the display unit 68 and the operating device 70 to operate interactively the apparatus.

Figure 2:
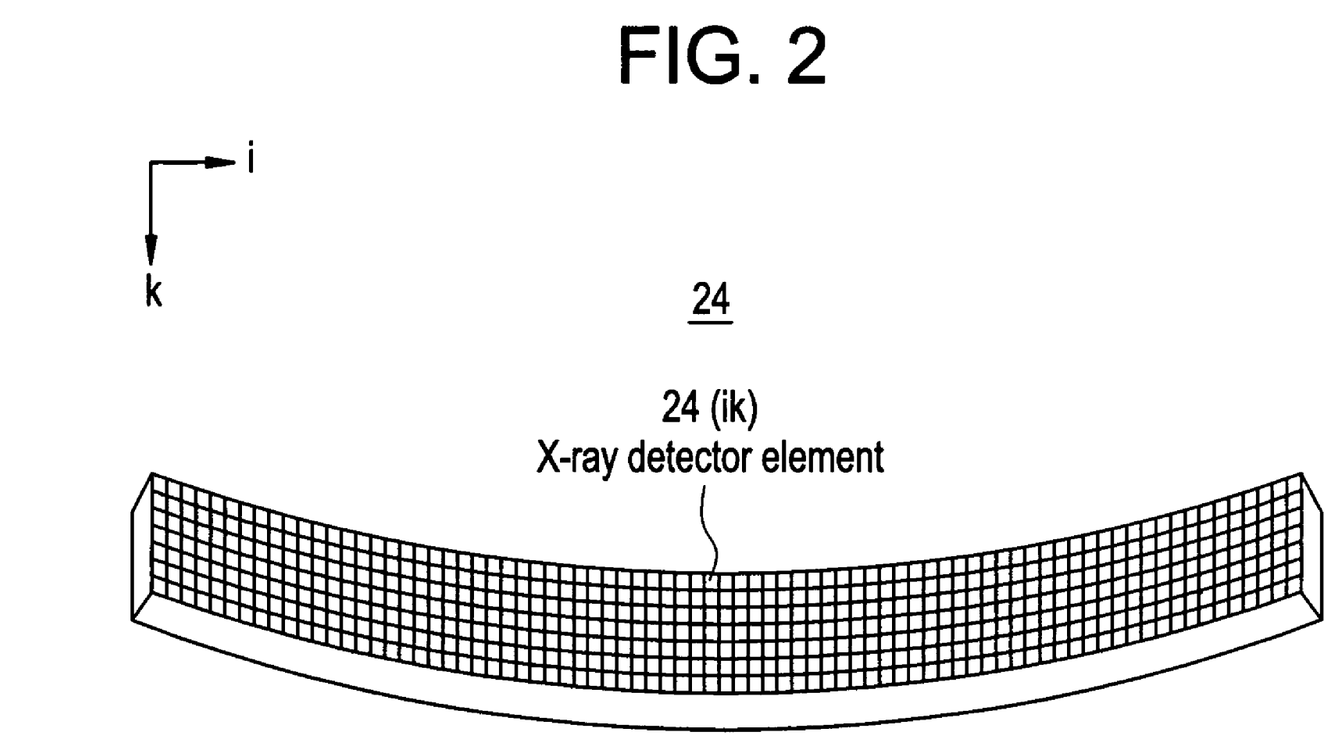
FIG. 2 is a schematic structure of an X-ray detector.

A schematic structure of an X-ray detector 24 is shown in FIG. 2. As shown in the figure, the X-ray detector 24 is a multichannel X-ray beam detector having a plurality of X-ray detector elements 24 (ik) arranged in a two dimensional array. The plurality of X-ray detector elements 24 (ik) forms an X-ray receiving facet curved in a cylindrical concave form.

"i" indicates the channel number, for example i=1, 2, ..., 1,000. "k" indicates the raw number, form example k=1, 2, ..., 32. In the X-ray detector 24 (ik) elements having the same raw number k forms a detector element array. The number of detector element array of the X-ray detector 24 may not be considered to be limited to 32, but may be an appropriate plural number.

An X-ray detector 24 (ik) is formed by the combination of for example a scintillator and a photo diode. The detector unit may not be limited thereto, but may be any other forms such as a semiconductor X-ray detector element using Cadmium-Tellur (CdTe), or an ion chamber type X-ray detector unit using Xenon gas.

Figure 3A:
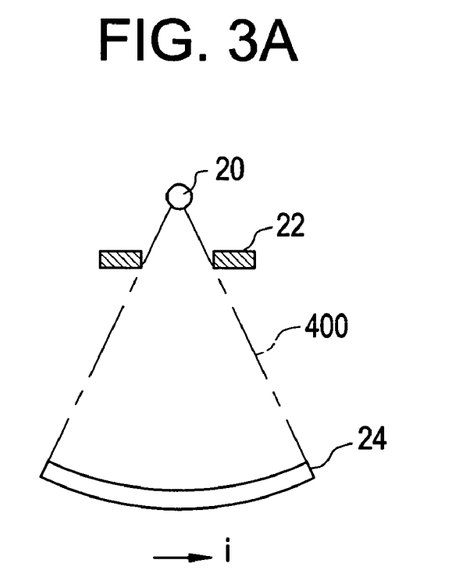
FIG. 3 is a schematic diagram of an X-ray radiation and detection system.
Figure 3B:
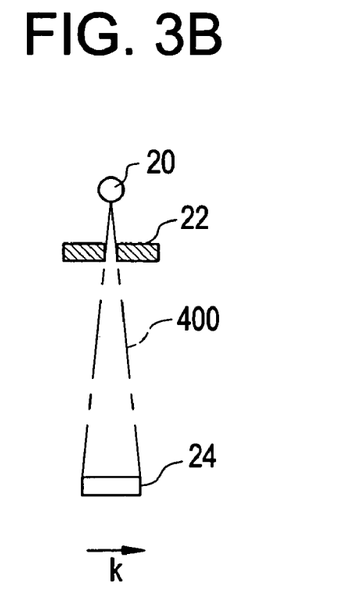

FIG. 3 shows the relationship between the X-ray tube 20, the collimator 22 and the X-ray detector 24 in the X-ray radiation and detection system. FIG. 3(a) is a schematic diagram illustrating a front view of the scanning gantry 2, FIG. 3(b) is a side view. As shown in the figure, the X-ray beam emitted from the X-ray tube 20 is formed to a cone shaped X-ray beam 400 by the collimator 22 to irradiate on the X-ray detector 24.

FIG. 3(a) illustrate the diversion of the cone shaped X-ray beam 400 in a direction. This direction will be referred to as the width direction herein below. The width of the cone shaped X-ray beam 400 matches the array direction of channels in the X-ray detector 24. In FIG. 3(b) there is shown an extension of the cone shaped X-ray beam 400 in another direction. This direction will be referred to as the thickness direction of X-ray beam 400 herein below. The thickness of the cone shaped X-ray beam 400 matches to the direction of apposition of a plurality of detector element arrays in the X-ray detector 24. Two directions of extension of the X-ray beam 400 are orthogonal to each other.

Figure 4:
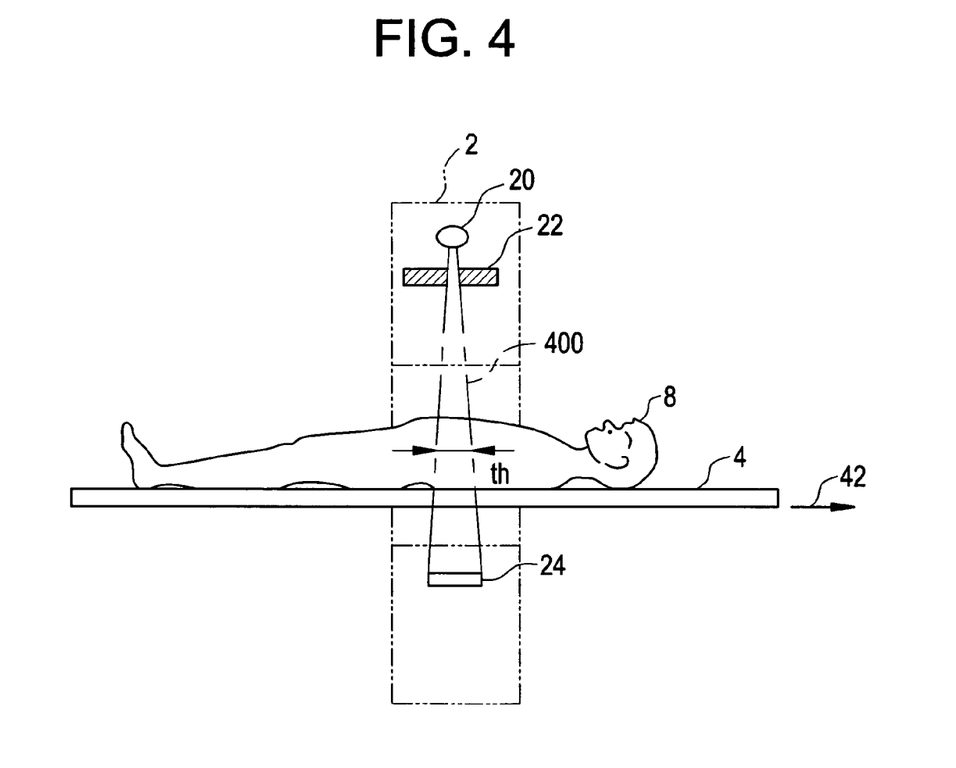
FIG. 4 is a schematic diagram illustrating the relationship between the X-ray radiation and detection system and the subject.

As shown in FIG. 4, the subject 8 mounted on the imaging table 4 is carried in to the X-ray radiation space so as to cross the body axis over the cone shaped X-ray beam 400. The scanning gantry 2 has a cylindrical structure containing the X-ray radiation and detection system therein.

The X-ray radiation space is formed in an inner space of the cylindrical structure of the scanning gantry 2. The sliced image of the subject 8 using the X-ray beam 400 is projected to the X-ray detector 24. The X-ray detector 24 detects X-ray transmitted through the subject 8 for each detector array. The thickness of the X-ray beam 400 radiated to the subject 8 is controlled by the opening of an aperture of the collimator 22.

In parallel to the revolution of the X-ray radiation and detection system, continuous movement of the imaging table 4 in the body axis of the subject 8 as shown by the arrow 42 allows the X-ray radiation and detection system to spin on the helical trajectory around the subject 8 in relation to the subject 8. This results in a so-called "helical scan".

For one turn of scan, a plurality of (for example, about approximately 1,000) views of projection data are gathered. The collection of the projection data is performed by the system including the X-ray detector 24, the data collector unit 26, and the data collector buffer 64. The projection data will be referred to as scan data herein below. Also the projection data in a view will be referred to as view data.

Figure 5:
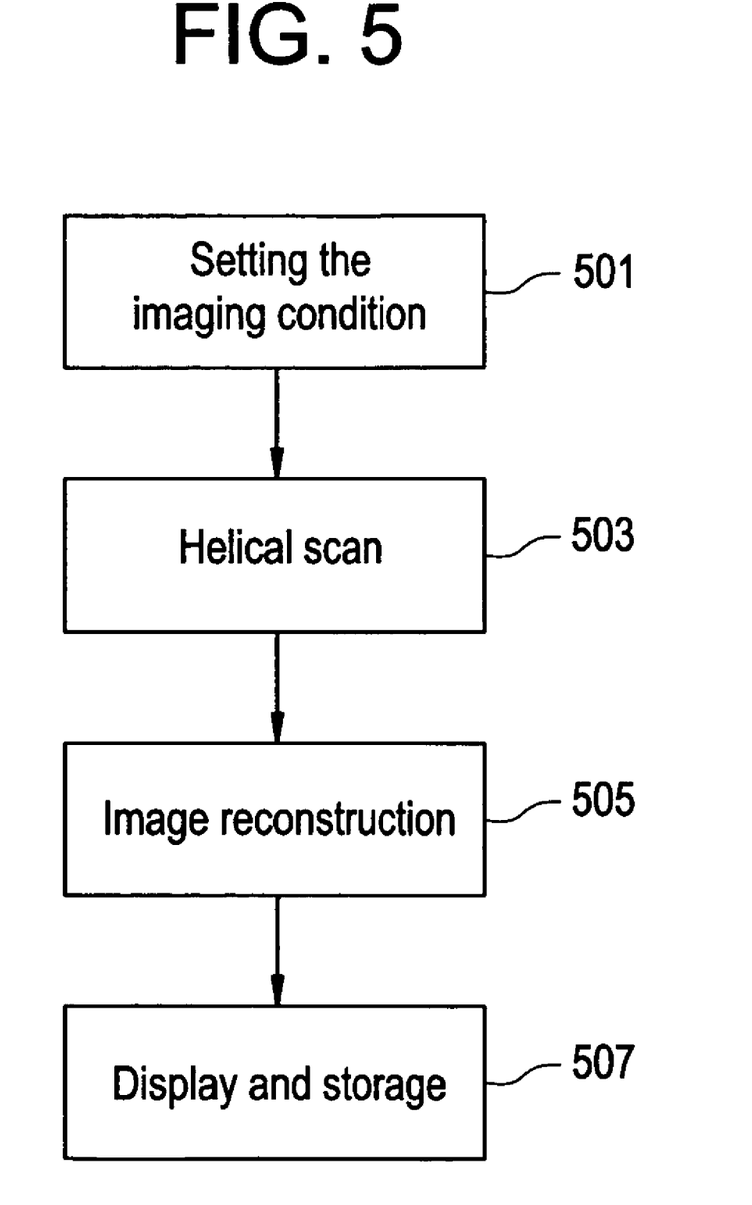
FIG. 5 is a flow chart illustrating the operation of an X-ray CT apparatus.

The operation of the apparatus will be described below. FIG. 5 shows the flow diagram of the operation of the apparatus. As shown in the figure, in stage 501 the scan imaging condition is configured. The details of how to determine the imaging condition will be described later.

Next, in stage 503, a helical scan is performed. The helical scan is performed in accordance with the imaging condition configured in stage 501, by the scanning gantry 2 and the imaging table 4. Then, in state 505, an image is reconstructed. The image reconstruction is performed by the data processing unit 60. The data processing unit 60 reconstructs the image using such method as the filtered back projection, based on the projection data collected by the helical scan. The reconstructed image is displayed and stored in stage 507. The image display is performed by the display device 60. The image storage is performed by the storage unit 66.

Figure 6:
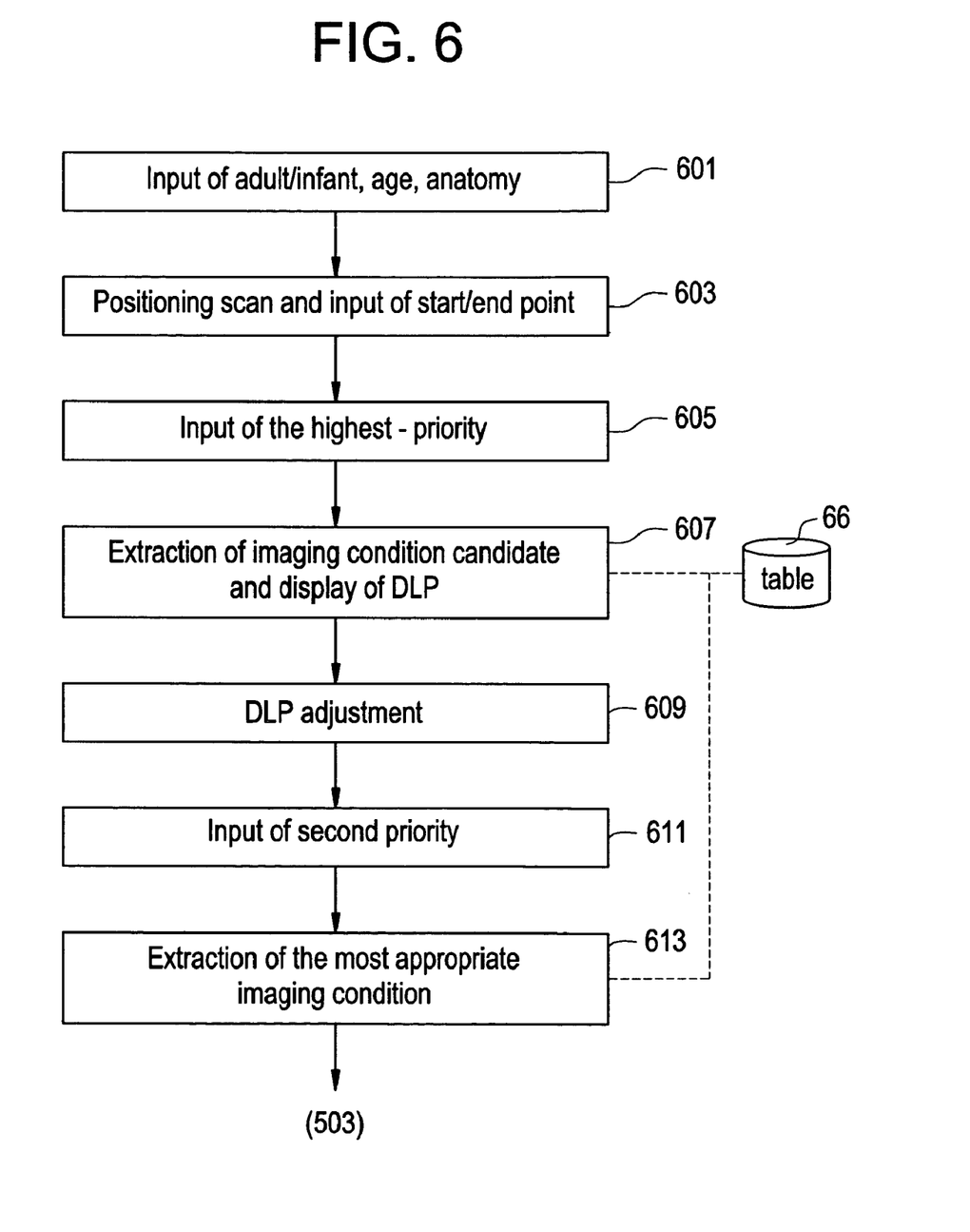
FIG. 6 is a flow chart illustrating the operation of an X-ray CT apparatus.

FIG. 6 shows a flow diagram of the imaging condition configuration. As shown in figure, in stage 601, inputs including adult/infant, age, and anatomy are set. The input of these data is performed by the operator through the operating device 70. Input in the following stages will be performed in the same manner. The adult input or infant input is selected according to whether the patient is adult or infant; the age of the patient is also input. The anatomy input will determine the desired imaging region such as the skull, eyeball, neck, chest, abdomen, legs and so on.

In stage 603, a positioning scan and start/end point input is performed. The positioning scan is performed by emitting the X-ray beam to the patient with the revolving scanning gantry 2 being stopped while the imaging table 4 is translated into the body axis of the patient. This results in a radioscopic image of the patient, or the scout image. In addition the mean X-ray amount for each position in the body axis is determined for the tube current auto control (auto mA). The start/end point input is performed by the operator using the radioscopic image to input the start point and end point of the helical scan. The imaging length of the helical scan is given by the start/end point input.

Next in stage 605, the highest-priority objective input is performed. The highest-priority objective is the most important purpose in the imaging of this patient, for example for a patient having very narrow tolerance to the exposure dose such as infants the exposure dose as low as possible is the top priority. For a patient having relatively large tolerance to the exposure dose such as adults, the image quality or the imaging speed may precede the dose. In the following description, the exposure dose may also be referred to as dose, image quality to IQ, imaging speed to speed.

The highest-priority objective may accept either dose, IQ or speed. The dose input is performed by numerical input of DLP (dose length product). Alternatively, the dose priority input is selected, indicating the dose as low as possible. For IQ and speed, IQ priority may be input indicative of the IQ as good as possible, or speed priority indicative of the speed as fast as possible.

Next, in stage 607, a candidate of imaging condition will be extracted and DLP will be displayed. The extraction of the candidate of imaging condition and DLP display are performed by the data processing unit 60. The data processing unit 60 extracts a candidate of imaging condition in accordance with the adult/infant, anatomy, imaging length, and the highest-priority from within the imaging condition table previously stored in the storage unit 66, and displays the DLP when imaging under the condition.

This DLP can be the default DLP in other words. When there are plural candidates of imaging condition, all of them are extracted, and a default DLP for each of them is displayed. The display of imaging condition candidates and default DLPs is performed on the display unit 68.

The imaging condition table is a table of various imaging condition sets, including various combinations of parameters such as tube voltage, tube current, beam thickness, helical pitch, slice thickness of the reconstructed image, filter used for image reconstruction and the like. The tube current is stored as the current profile in the body axis, obtained by the positioning scan in correspondence to the X-ray transmission in the body axis of the patient. The current profile is finer when the beam thickness is thinner, and broader when the beam thickness is thicker. The fine profile is more effective for decreasing the dose than the broad profile.

The imaging condition table as described above can be formed from the summary of the performance in the past. The table can also be formed through the simulation of various imaging condition.

Next, in stage 609, DLP is adjusted. The DLP adjustment is done by the user. The default DLP can be larger than the desired DLP, and in such a case the user adjust the displayed DLP to the desired value, using the operating device 70. Along with the DLP adjustment, the data processing unit 60 corrects the extracted image condition such that the DLP matches to the adjusted DLP. The correction of imaging condition is such that for example the amplitude of the tube current profile is decreased entirely. When the default DLP is less than the desired one, DLP is not be adjusted hence the imaging condition is not be corrected.

Next, in stage 611, second priority objective is input. The input of second priority objective is performed by the user. The second priority objective is the objective next to the highest-priority objective, and any one objective is input, which is not set to the highest-priority among the dose, IQ and speed. For example when the dose is the highest-priority, the second-priority objective can be IQ or speed. These are input as IQ priority or speed priority. The input of second priority objective may be omitted in some cases.

Next, in stage 613, the most appropriate imaging condition is extracted. The extraction of the most appropriate imaging condition is performed by the data processing unit 60. The data processing unit 60 extracts the imaging condition that matches to the second priority objective among candidates of imaging condition. The most suitable imaging condition among candidates of imaging condition is thereby extracted.

As can be appreciated from the foregoing description, after input of adult/infant, anatomy and start/end, it is sufficient to input the highest-priority and (if needed) second priority for automatic configuration of the most suitable imaging condition, without needs to input every parameters constituting the imaging condition, allowing the imaging condition to be determined very simply. In such an imaging condition the helical scan in the following stage 503 will be performed. By doing this the imaging result can achieve the highest-priority and second priority objectives.

Figure 7:
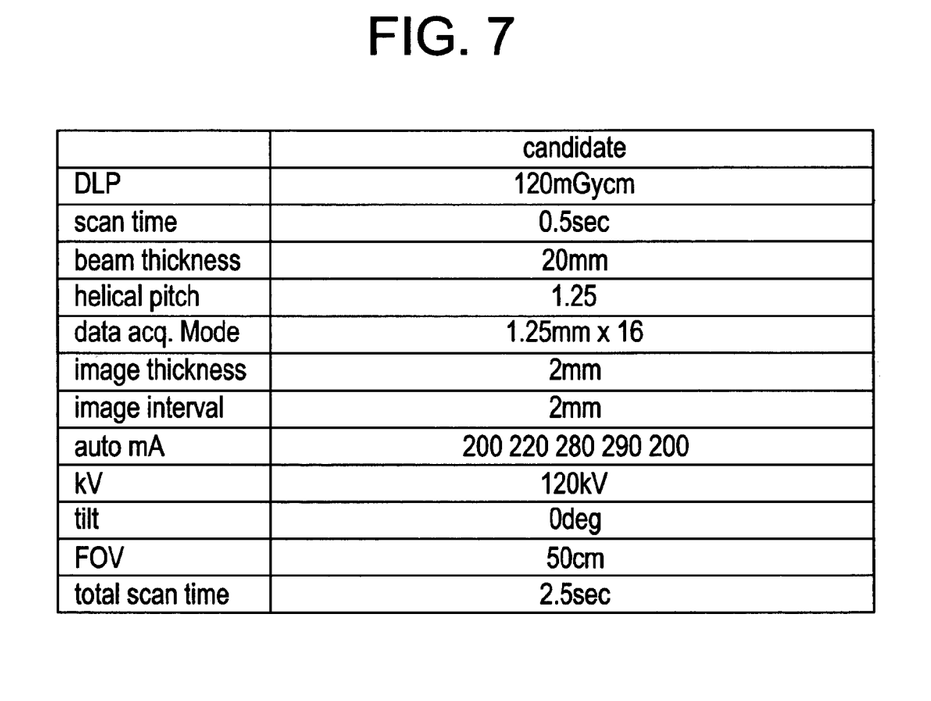
FIG. 7 is an exemplary display of imaging condition candidate.

FIG. 7 shows an exemplary display of imaging condition candidate and default DLP, both extracted along with the input of the highest-priority objective. It is assumed that DLP=100 mGycm is input for the highest-priority. With respect to this highest-priority the default DLP or an imaging condition candidate nearest thereto will be automatically extracted and displayed together with the default DLP.

At this point the default DLP value is 120 mGycm. For the scanning parameters constituting an imaging condition, for example, scanning time, beam thickness, helical pitch, data acquisition mode, image thickness, image interval, auto mA, tube voltage in kV, tilt angle, field of view (FOV), total scanning time are displayed.

Figure 8:
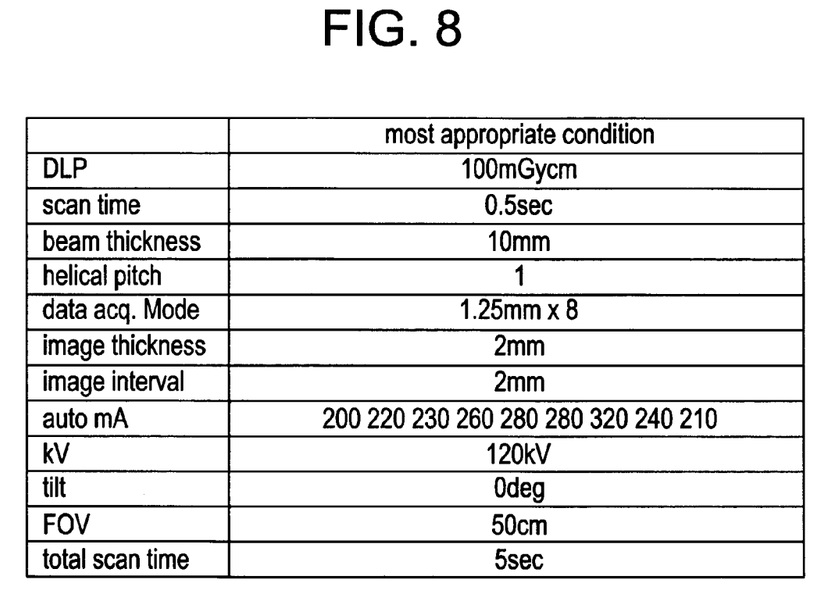
FIG. 8 is an exemplary display of most appropriate imaging condition.

For such an imaging condition candidate, by decreasing the default DLP to 100 mGycm to match to the highest-priority, the imaging condition candidate is corrected automatically in accordance thereto to obtain the most suitable imaging condition as shown in FIG. 8.

Figure 9:
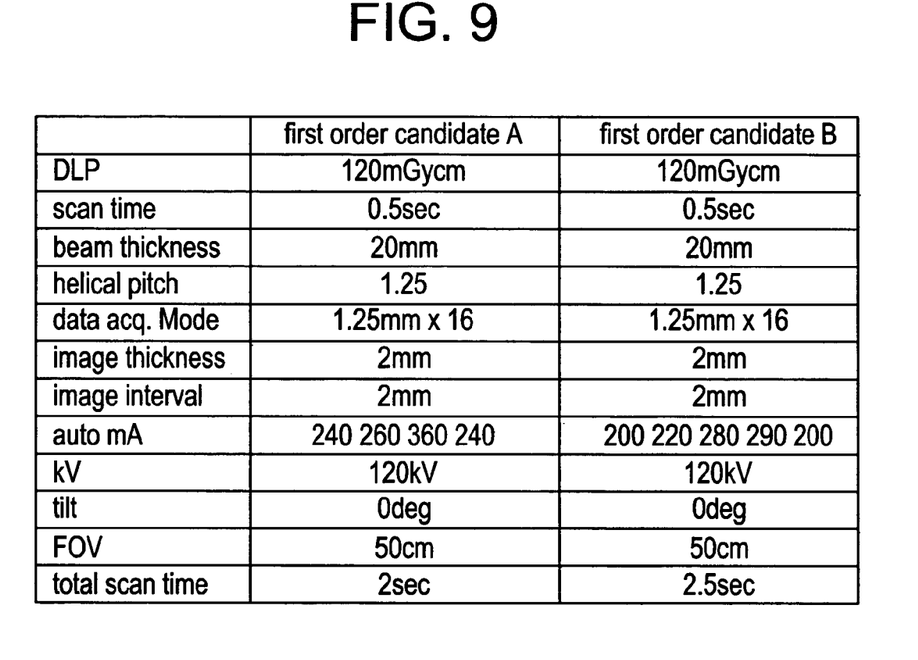
FIG. 9 is an exemplary display of imaging condition candidate.

FIG. 9 shows an example case in which two imaging condition candidates are extracted. The highest-priority is assumed that DLP=100 mGycm is input. For this highest-priority, the default DLP and two nearest candidates are automatically extracted and the candidates are displayed together with the default DLP. These candidates are the first order.

Figure 10:
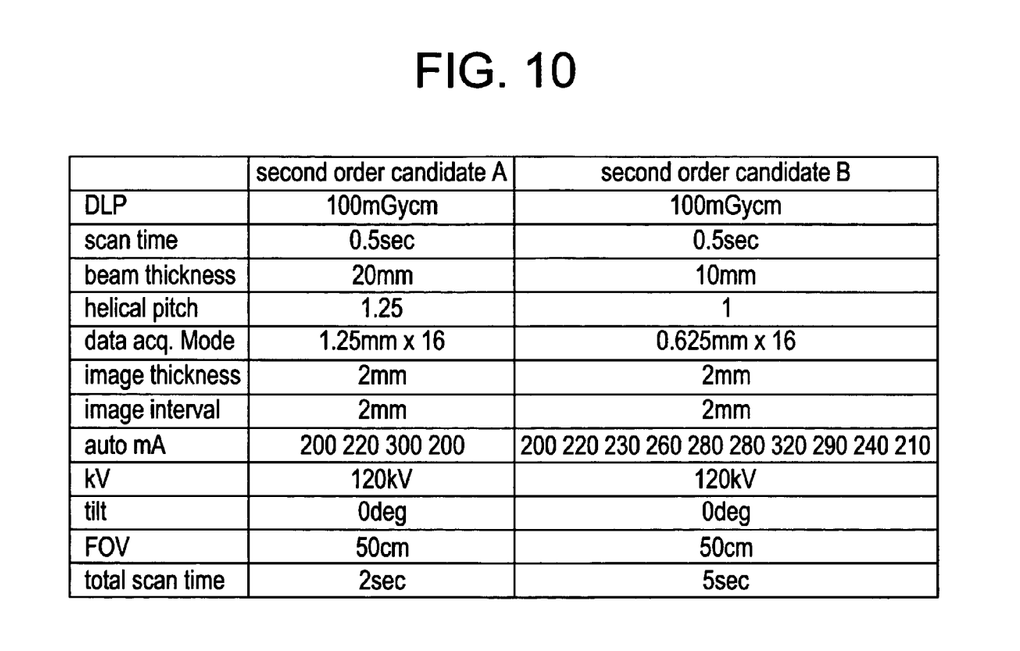
FIG. 10 is an exemplary display of imaging condition candidate.

The default DLP in both candidates is 120 mGycm. For those imaging condition candidates, when the default DLP is decreased to 100 mGycm to match to the highest-priority objective, the imaging condition candidates are automatically adjusted in accordance thereto, and the imaging condition as shown in FIG. 10 is displayed. These candidates are the second order.

From within those second order candidates, any one is automatically selected which conforms to the second priority to constitute the most suitable imaging condition. If speed is selected for the second priority the second order candidate A will be selected; if IQ is selected for the second priority the second order candidate B will be selected.

Many widely different embodiments of the invention may be constructed without departing from the spirit and the scope of the present invention. It should be understood that the present invention is not limited to the specific embodiments described in the specification, except as defined in the appended claims.

The invention claimed is:

1. An imaging condition determining method for an x-ray CT apparatus for performing imaging by a helical scan, comprising the steps of:
    making a table of various imaging conditions in advance;
    extracting a first candidate imaging condition from said table in accordance with an age, imaging region, imaging length of a patient, and the highest-priority objective specified by a user, and displaying an exposure dose of the patient under the first candidate of imaging condition;
    enabling the user to adjust said exposure dose; and
    determining a second candidate imaging condition adjusted in response to the adjustment of said exposure dose.

2. An imaging condition determining method according to claim 1, wherein said highest-priority objective is the exposure dose.

3. An imaging condition determining method according to claim 1, wherein said highest-priority objective is one of exposure dose, image quality, and imaging speed.

4. An imaging condition determining method according to claim 2, wherein said exposure dose is indicated as a dose length product (DLP).

5. An imaging condition determining method according to of claim 1, wherein when there are plural candidates of said imaging conditions, one of the imaging conditions is determined based on a second priority objective specified by the user.

6. An imaging condition determining method according to claim 5, wherein said second priority objective is one, which is different from the highest-priority objective, of the exposure dose, image quality and imaging speed.

7. An imaging condition determining method according to claim 1, wherein said imaging conditions contained in said table are the imaging conditions based on the performance.

8. An imaging condition determining method according to claim 1, wherein said imaging conditions contained in said table are the imaging conditions based on a simulation.

9. An X-ray CT apparatus, comprising:
    a memory device for storing a variety of imaging conditions previously made as a table;
    a display device for extracting a first candidate imaging condition from said table in accordance with an age, imaging region, imaging length of a patient, and the highest-priority objective specified by a user for displaying an exposure dose of the patient under the first candidate imaging condition;
    an adjusting device for enabling the user to adjust said exposure dose; and
    a determining device for determining a second candidate imaging condition by performing correction in response to the adjustment of said exposure dose.

10. An X-ray CT apparatus according to claim 9, wherein said highest-priority objective is the exposure dose.

11. An X-ray CT apparatus according to claim 9, wherein said highest-priority objective is any one of exposure dose, image quality, and imaging speed.

12. An X-ray CT apparatus according to claims 10, wherein said exposure dose is indicated as a dose length product (DLP).

13. An X-ray CT apparatus according to claim 9, wherein when there is a plurality of candidates of said imaging conditions, one of the imaging conditions is determined based on a second priority objective specified by the user.

14. An X-ray CT apparatus according to claim 13, wherein said second priority objective is one, which is different from the highest-priority objective, of the exposure dose, image quality and imaging speed.

15. An X-ray CT apparatus according to claim 9, wherein said imaging conditions contained in said table are imaging conditions based on the performance.

16. An X-ray tomographic imaging helical scan CT apparatus according to claim 9 in which:
    said imaging conditions contained in said table are imaging conditions based on a simulation.

* * * * *